US012041992B2

(12) United States Patent
Magee

(10) Patent No.: US 12,041,992 B2
(45) Date of Patent: Jul. 23, 2024

(54) DIFFUSER HEADBAND SYSTEM FOR 360 DEGREES OF AIR DISTRIBUTION

(71) Applicant: Florida A&M University, Tallahassee, FL (US)

(72) Inventor: Charles Magee, Cairo, GA (US)

(73) Assignee: Florida A&M University, Tallahassee, FL (US)

( * ) Notice: Subject to any disclaimer, the term of this patent is extended or adjusted under 35 U.S.C. 154(b) by 449 days.

(21) Appl. No.: 17/403,722

(22) Filed: Aug. 16, 2021

(65) Prior Publication Data

US 2022/0053856 A1     Feb. 24, 2022

Related U.S. Application Data

(60) Provisional application No. 63/067,049, filed on Aug. 18, 2020.

(51) Int. Cl.
*A61L 9/00*         (2006.01)
*A41D 20/00*      (2006.01)
*A61L 9/015*       (2006.01)

(52) U.S. Cl.
CPC ............ *A41D 20/005* (2013.01); *A61L 9/015* (2013.01); *A61L 2209/15* (2013.01)

(58) Field of Classification Search
CPC ...................................................... A61L 9/015
See application file for complete search history.

(56) References Cited

U.S. PATENT DOCUMENTS 2,773,262 A * 12/1956 Brouha .............. A41D 13/0025
2/81

* cited by examiner

*Primary Examiner* — Robert A Hopkins
(74) *Attorney, Agent, or Firm* — Greenberg Traurig, LLP

(57) ABSTRACT

Various embodiments are directed to a diffuser headband system. The system may include a diffuser headband formed from an elastic material coupled to a sanitized air generating source that produces sanitized air. The diffuser headband may form a substantially oval shape and include an elastic tube attached to the elastic material. A first portion of the elastic tube may be perforated to include a group of air outlet holes spaced along a surface of the elastic tube. A second portion of the elastic tube may include an inlet that receives the sanitized air from the sanitized air generating source. The air outlet holes receive the sanitized air from the inlet and expel the sanitized air to provide an air shield that encircles a person's body wearing the diffuser headband. The air shield blocks viral aerosol droplets from entering or leaving an airspace occupied by the person wearing the diffuser headband.

14 Claims, 3 Drawing Sheets

DIFFUSER HEADBAND SYSTEM FOR 360 DEGREES OF AIR DISTRIBUTION

CROSS REFERENCE TO RELATED APPLICATION

This application claims the benefit of U.S. Provisional Application No. 63/067,049, filed Aug. 18, 2020, the disclosure of which is incorporated, in its entirety, by this reference.

BACKGROUND

The world is currently in the midst of the worse pandemic in more than 100 years due to the coronavirus (COVID-19) which is a contagious disease caused by severe acute respiratory syndrome coronavirus 2 (SARS-CoV-2). While there are currently experimental vaccines available protecting persons from becoming sick from COVID-19, there is still uncertainty within the medical community regarding their effectiveness in preventing transmission of the virus. Furthermore, at the present time there is no known cure and it has become evident that COVID-19 will persist for a very long time.

Scientists now understand that the novel coronavirus (i.e., SARS-CoV-2), which causes COVID-19, may be spread by hitching a ride inside large respiratory droplets that are expelled as airborne particles when someone coughs, sneezes, sings, or talks. There is also some evidence that smaller droplets from breathing can also spread the virus as airborne particles known as aerosols. Many scientists also believe that these aerosols are tiny enough that they may remain suspended in the air, float around, be pushed by air current, and accumulate in enclosed spaces, such as households. Scientists have also been determined that people do not emit equal amounts of aerosols during every activity. For example, singing emits more aerosols than breathing. Additionally, it has been determined that some people may be super-emitters (i.e., super-spreaders) of aerosols and that most super-spreader events occur at indoor venues (especially those with poor ventilation) where large numbers of people are talking, chanting, or singing. Examples of indoor venues where super-spreader events have previously taken place include restaurants, bars, clubs, choir practices, weddings, funerals, cruise ships, nursing homes, prisons, and meatpacking plants.

The Centers for Disease Control and Prevention (CDC) has issued recommendations for mitigating the spread of aerosols carrying COVID-19 including maintaining social distancing (e.g., staying at least six feet apart from other persons) and wearing a face mask and/or shield. However, it has become apparent that some people are unwilling to abide by the CDC's recommendations despite these recommendations being made for their safety and the safety of others. Moreover, in some venues, high-efficiency particulate air (HEPA) filter cleaners may be utilized to catch tiny aerosols that may be carrying the coronavirus. However, most heating, ventilation, and air conditioning (HVAC) systems utilized by indoor venues do not use HEPA filters because they are too expensive, thereby enabling viral-laden aerosols to be spread by the HVAC systems utilized in these indoor venues.

SUMMARY

As will be described in greater detail below, the instant disclosure generally relates to a diffuser headband system for 360 degrees of air distribution. In one example, the system may include a diffuser headband formed from an elastic material coupled to a sanitized air generating source that produces sanitized air. The diffuser headband may form a substantially oval shape and include an elastic tube attached to the elastic material. A first portion of the elastic tube may be perforated to include a group of air outlet holes spaced along a surface of the elastic tube. A second portion of the elastic tube may include an inlet that is coupled to an outlet of the sanitized air generating source and that receives the sanitized air from the sanitized air generating source. The air outlet holes may receive the sanitized air from the inlet and expel the sanitized air to provide an air shield that encircles a person's body wearing the diffuser headband. The air shield blocks viral aerosol droplets from entering or leaving an airspace occupied by the person wearing the diffuser headband. In some examples, the air shield generated by the system described herein may also block airborne bacteria and/or spores from entering or leaving an airspace occupied by the person wearing the diffuser headband.

In some examples, the sanitized air generating source in the system described herein may be a portable cooling apparatus, such as a solar adiabatic cooling vest, that may be worn by the person wearing the diffuser headband and that generates the sanitized air. In other examples, the sanitized air generating source may be an air distribution apparatus (e.g., an air sanitizing hood) that generates the sanitized air from above an enclosed space (e.g., a room or attic ceiling) occupied by one or more persons wearing the diffuser headband. In some examples the air distribution apparatus may be coupled to one or more diffusers each including a perforated elastic tube. The perforated elastic tube may include a group of apertures spaced along a substantial portion of a surface of the elastic tube. The perforated elastic tube may further include an inlet that receives the sanitized air from an outlet of the air distribution apparatus. The received sanitized air may be expelled through the group of apertures to provide another air shield that blocks a spread of the aerosol droplets within an enclosed space below the air distribution apparatus. In some examples, the diffusers coupled to the air distribution apparatus may form a substantially oval shape and be capable of swiveling about a horizontal and/or a vertical axis.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

DETAILED DESCRIPTION

Figure 1A:
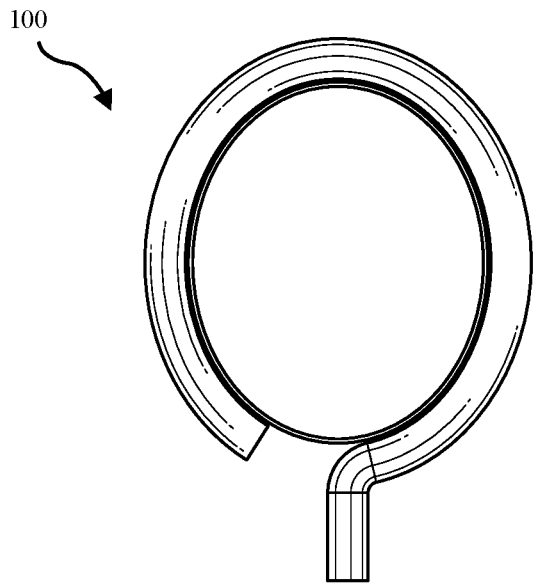
FIG. 1A illustrates a top view of a diffuser headband, according to an example embodiment.

The present disclosure is generally directed to a diffuser headband system for 360 degrees of air distribution. In the various embodiments described herein, the diffuser headband system may be provided for preventing large and small droplets from falling onto a person's mouth, nose, eyes, or body, especially in an indoor venue where super-spreader events are likely to occur. In some venues, high-efficiency particulate air (HEPA) filter cleaners may be utilized to catch tiny aerosols that may be carrying viruses (e.g., the coronavirus). However, most heating, ventilation, and air conditioning (HVAC) systems utilized by indoor venues do not use HEPA filters because they are too expensive, thereby enabling viral-laden aerosols to be spread by the HVAC systems utilized in these indoor venues. As will be described in greater detail below, the various embodiments of the system described herein may include a diffuser headband which may be constructed from an elastic headband (which may be worn on a person's head) and an elastic tube that is perforated with a group of air outlet holes evenly spaced along a portion of the tube's length to provide a 360-degree wall (i.e., a shield) of air around a person's body thereby blocking any viral droplets from spreading from or entering onto a person's mouth, nose, eyes, or body. Another portion of the elastic tube may include an air inlet. The air inlet may be connected to the outlet of a cooling apparatus that generates sanitized air (i.e., air from which virus-laden aerosols, airborne bacteria, and/or airborne spores have been removed). The sanitized air may be received in the air inlet from the cooling apparatus outlet and then dispersed through the group of air outlet holes to provide the 360-degree air shield.

In some embodiments, the cooling apparatus may include technology that generates sanitized air by capturing, killing, and/or destroying harmful microorganisms in indoor and outdoor air. For example, an exemplary cooling apparatus may include a sanitized air generating source such as a solar adiabatic cooling apparatus, which is described in U.S. Pat. No. 10,222,113, the disclosure of which is incorporated, in its entirety, herein. For example, and as will be described in greater detail herein, a diffuser headband may be connected to the outlet of a solar adiabatic cooling apparatus worn on the body of a person (e.g., as a vest) to receive sanitized air. In another embodiment, the cooling apparatus may include a sanitizing hood containing an air distribution duct that generates sanitized air through a number of air outlets (e.g., port holes) capable of connecting to the air inlet of a diffuser headband worn by a person. The air outlets of the sanitizing hood may additionally include direct connections (e.g., fixed connections or swivel connections) to one or more diffusers containing air outlet holes for circulating the sanitized air within an enclosed space occupied by one or more persons. In some examples, the circulated sanitized air may be received through the air outlet holes of unconnected diffuser headbands (i.e., diffuser headbands where the air inlet is uncoupled to an outlet) worn by one or more persons in the enclosed space.

The various embodiments of the diffuser headband system disclosed herein are applicable to a plethora of professions and virus super-spreader events where at least six feet of social distancing cannot be achieved and separation from clientele is needed or required such as professions in the fields of education, health care, entertainment, and transportation (among others). For example, in the transportation industry, there is a need for bus drivers to be separated from their riders. Similarly, in the field of education, there is a need for teachers need to be isolated from their students.

By utilizing the system as described above, various advantages may be realized for destroying harmful microorganisms (e.g., the coronavirus and/or other viruses, bacteria, and/or spores) carried within airborne particles or aerosols in both indoor and outdoor airstreams. These advantages may include, without limitation, (1) shielding a person's body from virus-laden aerosol droplets, (2) mitigating the spread of COVID-19 in both indoor and outdoor environments, (3) eliminating the need to wear a mask or shield when the diffuser headband system is utilized, (4) constructing a diffuser headband using washable materials thereby allowing reuse, (5) enabling the capture, killing, and destruction of viruses, bacteria, and spores in recirculated air, (6) permitting constant sanitization of recirculated air in an enclosed venue, (7) allowing social-distancing space to be reduced by 50% or more, (8) enabling the diffuser headband to be worn as a fashion item, (9) allowing for a fragrance to be added to the recirculated air provided by the diffuser headband system, (10) allowing health care workers to be isolated from sick patients and sick patients to be isolated from each other, (11) allow people to stay cool in a hot environment from the air generated by the diffuser headband system, (12) making it possible for schools and colleges/universities to open in a much safer environment, (13) allowing bus drivers to be isolated from their riders, (14) allowing secretaries/administrative assistants/receptionists to be isolated from visitors, (15) allowing persons seated at a table to be shielded from projected droplets and aerosols, (16) enabling the diffuser headband system to be operated using alternating current (AC), direct current (DC), or solar power, (17) quickly sanitizing a large volume of air, (18) allowing bartenders to be isolated from their customers, (19) providing protection against projected droplets and aerosols so that people can safely attend indoor and/or outdoor sporting events, (20) mitigating the spread of COVID-19 at super-spreader events in a variety of venues including restaurants, bars, clubs, choir practices, wedding, funerals, cruise ships, nursing homes, prisons, and meatpacking plants, and (21) allowing teachers to have freedom of movement in classroom and/or laboratory environments.

Embodiments of the disclosure now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1B:
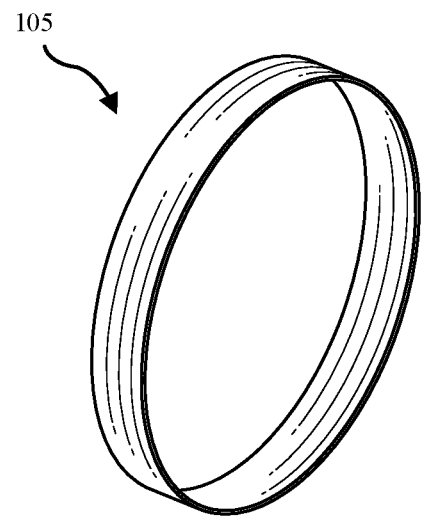
FIG. 1B illustrates an elastic headband portion of the diffuser headband shown in FIG. 1A, according to an example embodiment.
Figure 1C:
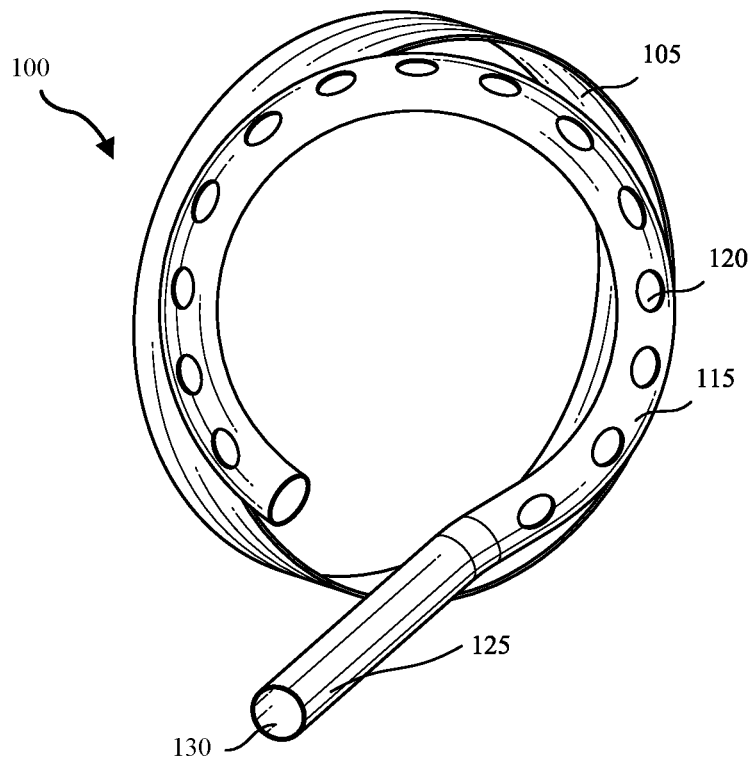
FIG. 1C illustrates a perspective view of a diffuser headband, according to an example embodiment.

FIG. 1A illustrates a top view of a diffuser headband 100, according to an example embodiment. In some embodiments, diffuser headband 100 may be constructed from a perforated elastic tube 115 (as shown in FIG. 1C) and an elastic headband 105 (as shown in FIGS. 1B and 1C). In some examples, elastic headband 105 may be washable and reusable. As shown in FIG. 1C, perforated elastic tube 115 may include a group of evenly spaced air outlet holes 120 (i.e., apertures) and an air inlet 125 that receives sanitized air through opening 130. As will be described in greater detail below, air received by air inlet 125 may be evenly distributed through air outlet holes 120 to create a 360-degree wall of air (i.e., an air shield) around a person's body.

Figure 2:
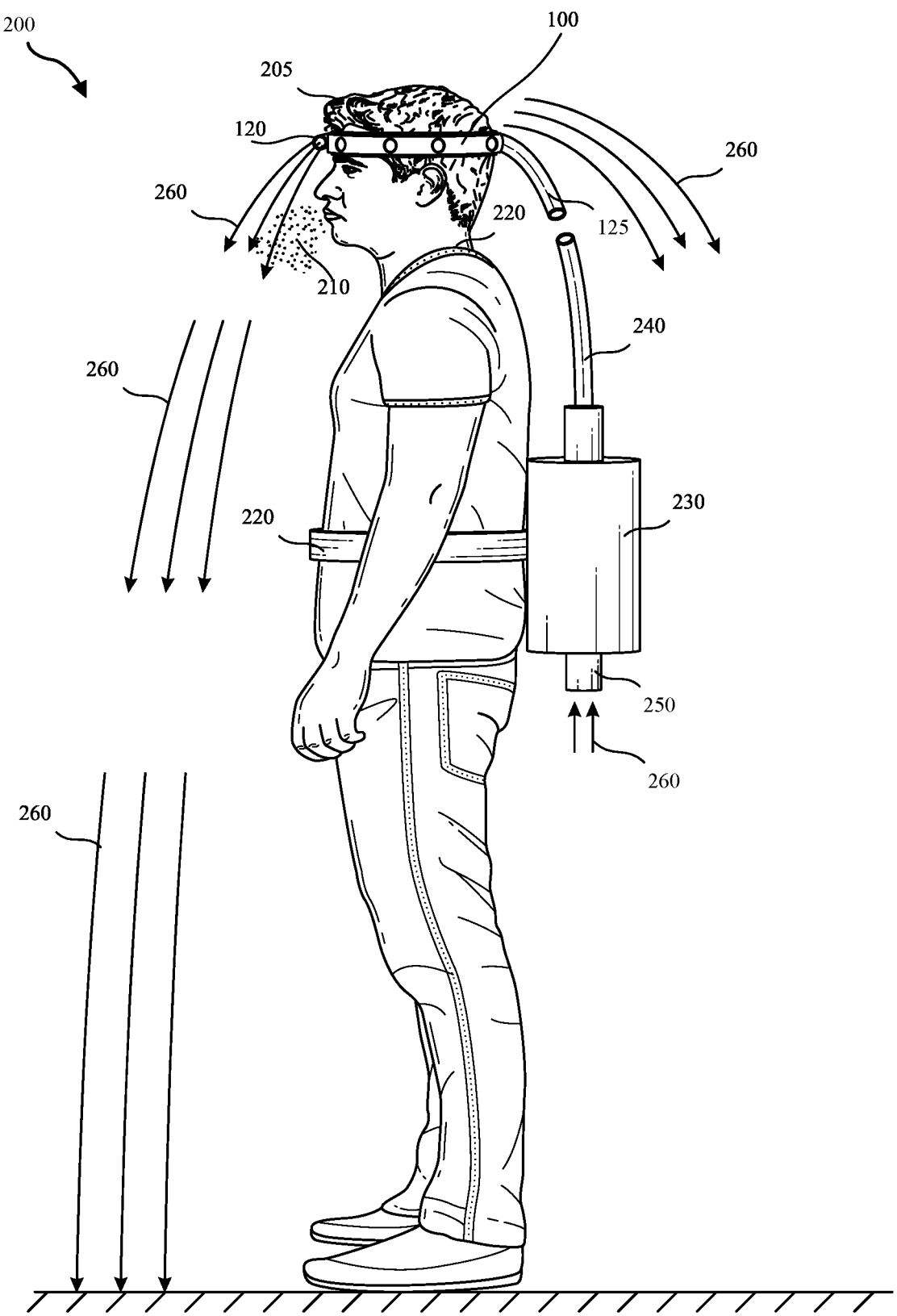
FIG. 2 illustrates a left-side view of a diffuser headband system utilizing a portable cooling apparatus, according to an example embodiment.

FIG. 2 illustrates a left-side view of a diffuser headband system 200 utilizing a portable cooling apparatus 230 adapted to generate sanitized air such that is functions as a sanitized air generating source, according to an example embodiment. In some embodiments, diffuser headband system 200 may include diffuser headband 100 (as described above with respect to FIGS. 1A-1C) that may be attached to the head of a person 205. Diffuser headband system 200 further includes portable cooling apparatus 230 that may be attached to person 205 (e.g., as a vest) via straps 220. In some embodiments, portable cooling apparatus 230 may be connected to air inlet 125 of diffuser headband 100 utilizing air outlet 240. Portable cooling apparatus 230 may further include air inlet 250 that receives, recirculates, and sanitizes air. Air inlet 125 may receive sanitized air as air jets 260 and distribute air jets 260 through air outlet holes 120 to create a 360-degree air shield around the body of person 205 such that virus laden droplets 210 generated by person 205 inside of the air shield or suspended in the air outside of the air shield are blocked. Furthermore, any virus laden air contained in the space occupied by person 205 may be recirculated through portable cooling apparatus 230 and sanitized.

In some embodiments, portable cooling apparatus 230 may be a solar adiabatic cooling vest (as described in U.S. Pat. No. 10,222,113) adapted to generate sanitized air by saturating a wick material with a saline and soap solution, whereby salt molecules within the saline and soap solution attract airborne droplets contaminated with a virus and soap molecules within the saline and soap solution react with the airborne droplets to dissolve a fatty layer of virus cell membranes, thereby destroying the virus. In one example, the solar adiabatic cooling vest may utilize adiabatic evaporation to cool hot, dry air. Hot outside humid air is drawn by an exhaust fan through an air inlet over large particles of salt to lower the air humidity before passing through the saturated wick material resulting in any airborne virus droplets being destroyed and sanitizing the air. Heat in the air evaporates water in the saturated wick material, thus causing the sanitized air leaving the wick material to be saturated and at a lower temperature than the incoming air. The saturated and sanitized air passes through a salt filter to lower the sanitized air's relative humidity. After exiting the salt filter, the cooled, drier sanitized air passes through an air filter to further lower its humidity and remove any salt particles from the sanitized air.

Figure 3:
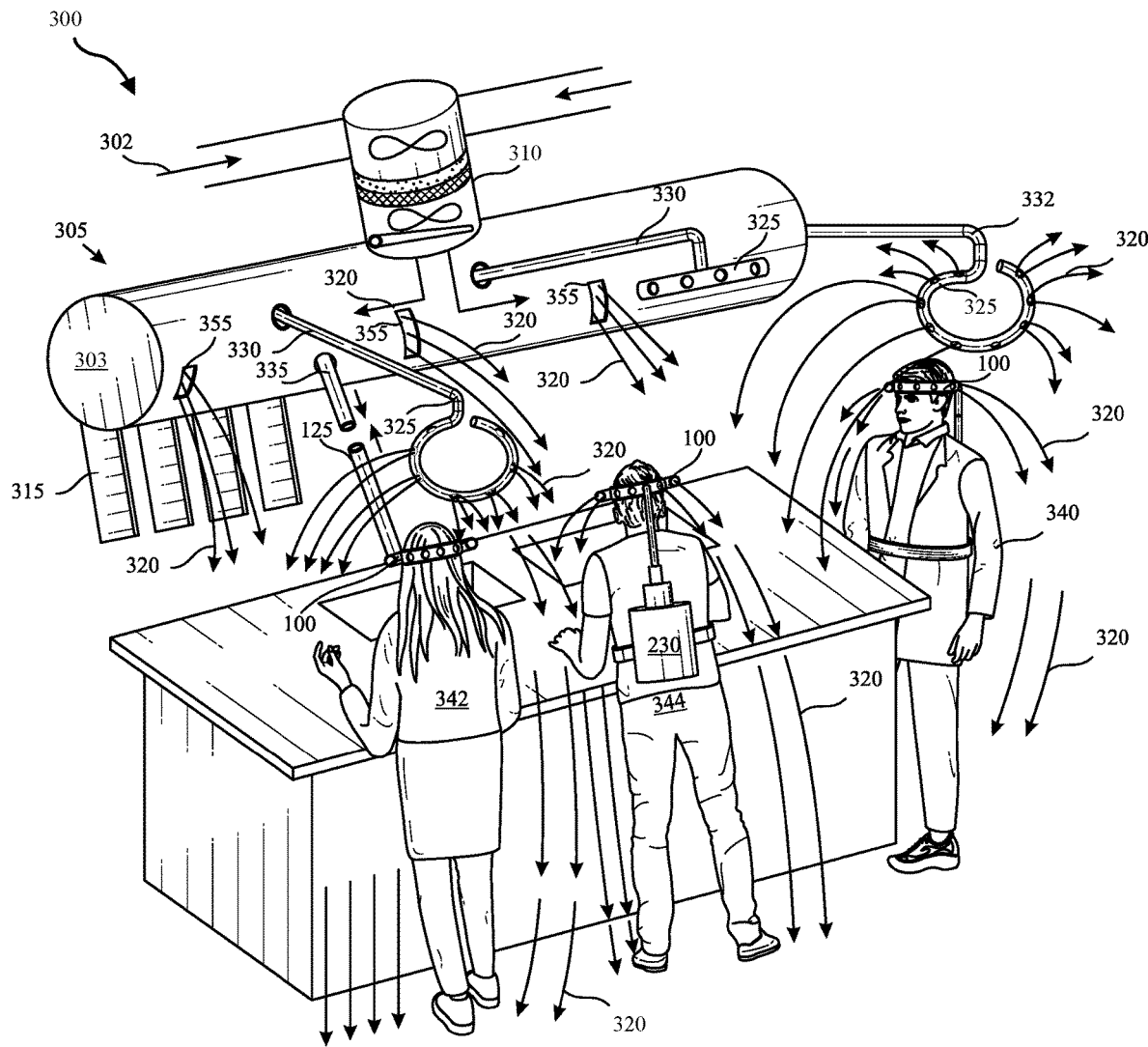
FIG. 3 illustrates a perspective view of a diffuser headband system utilizing a sanitizing hood, according to an example embodiment.

FIG. 3 illustrates a perspective view of a diffuser headband system 300 utilizing an air sanitizing hood 305, according to an example embodiment. In some embodiments, diffuser headband system 300 may be utilized in an enclosed space (e.g., a science classroom or laboratory) occupied by a teacher 340 and students 342 and 344. As shown in FIG. 3, diffuser headband system 300 may include an air sanitizing hood 305 that may be suspended from a ceiling of an enclosed space or alternatively, be installed within an attic above the ceiling of an enclosed space in a building, to provide sanitized air in the form of air jets 320 from one or more attached diffusers 325 as well as from port holes 355.

In some embodiments, air sanitizing hood 305 may include a distribution duct 303, an anti-virus guard 315 and a sanitization component 310. In some examples, anti-virus guard 315 and sanitation component 310 may function to sanitize inlet air 302 for distribution as air jets 320 from distribution duct 303. For example, sanitization component 310 may include various sub-components such as, without limitation, ventilation fans, a salt filter, an electro-static filter, and one or more UV light sources capable of destroying virus-laden droplets that may be present in inlet air 302. Additionally, anti-virus guard 315 may include a set of strips coated with a saline and soap solution for attracting virus-laden droplets. Then, via osmosis, water may be drawn from the droplets and the virus cells contained therein. Next, soap molecules on anti-virus guard 315 react to dissolve the fatty layer of the virus thus destroying its ability to replicate in a cell.

In some examples, each of diffusers 325 on air sanitizing hood 305 may include a group of evenly spaced diffuser and an air inlet for receiving and distributing the sanitized air provided by air sanitizing hood 305. In some examples, diffusers 325 may be attached to air sanitizing hood 305 via fixed connection arms 330 (or optionally via swivel arm 332) that extend diffusers 325 over an enclosed space so that sanitized air from each diffuser 325 may be distributed overhead as a 360-degree air shield over an area (e.g., a laboratory workbench) occupied by teacher 340, student 342, and/or student 344. As a result, teacher 340, student 342, and/or student 344 may enjoy freedom of movement around the enclosed space and maintain protection from virus-laden aerosols. In some embodiments, fixed connection arms 330 and swivel arm 332 may also function as the air inlets for diffusers 325. In some embodiments, air sanitizing hood 305 may additionally include an air outlet 335 for connecting to the air inlet of a diffuser headband (e.g., air inlet 125 of diffuser headband 100 worn by student 342).

In some embodiments, teacher 340 and students 342 and 344 may wear a diffuser headband 100 (as described above with respect to FIGS. 1A-1C). Additionally, diffuser headband 100 worn by student 344 may also be connected to a portable cooling apparatus 230 (as described above with respect to FIG. 2) from which sanitized air is received into the diffuser of diffuser headband 100 to create a 360-degree air shield, in the form of air jets 320, around the body of student 344. The air shield formed by air jets 320 may serve as a "wall" such that virus laden droplets generated by student 344 inside of the air shield or suspended in the air outside of the air shield are blocked (i.e., prevented from reaching the mouth, nose, eyes, or body of student 342 and teacher 340). Additionally, diffuser headband 100 worn by teacher 340 may also be connected to a separate portable cooling apparatus 230 (not shown) for receiving air jets 320 into the diffuser of diffuser headband 100 to create the air shield as described above around the body of teacher 340. Additionally, in some embodiments, diffuser headband 100 worn by student 342 may not be connected to air sanitizing hood 305 but a diffuser 325 may distribute air jets 320 through its air outlet holes to create the air shield as described above around the body of student 342. Optionally (and as discussed above), student 342 may connect air inlet 125 of diffuser headband 100 to air outlet 335 of air sanitizing hood 305 so that the air jets 320 may be provided through the diffuser of diffuser headband 100 to create the air shield as described above around the body of student 342.

Any process parameters and sequence of steps described and/or illustrated herein are given by way of example only and can be varied as desired. For example, while steps illustrated and/or described herein may be shown or discussed in a particular order, these steps do not necessarily need to be performed in the order illustrated or discussed. Additionally, any exemplary methods described and/or illustrated herein may also omit one or more of steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A diffuser headband system, comprising:
    a sanitized air generating source that produces sanitized air, wherein the sanitized air generating source comprises an air distribution apparatus coupled to one or more diffusers, the one or more diffusers comprising a perforated elastic tube, the perforated elastic tube comprising a plurality of apertures spaced along a surface of the elastic tube, the perforated elastic tube further comprising an inlet that receives the sanitized air from an outlet of the air distribution apparatus, wherein the plurality of apertures expel the sanitized air in a generally downward direction to provide an air shield by creating a 360-degree wall of air below the air distribution apparatus; and
    a diffuser headband formed from an elastic material comprising a substantially oval shape and an elastic tube attached to the elastic material, wherein a first portion of the elastic tube comprises a plurality of apertures spaced along a surface of the elastic tube, wherein a second portion of the elastic tube, detachably coupled to the sanitized air generating source, comprises an inlet that receives the sanitized air from the sanitized air generating source, wherein the plurality of apertures receive the sanitized air from the inlet and expel the sanitized air to provide an air shield that encircles a body of a person wearing the diffuser headband by creating another 360-degree wall of air, and wherein the air shield blocks aerosol droplets generated by the person wearing the diffuser headband.

2. The system of claim 1, wherein the air shield further blocks aerosol droplets within an enclosed space outside of air shield from reaching the person wearing the diffuser headband.

3. The system of claim 1, wherein the inlet of the elastic tube is coupled to an outlet of the sanitized air generating source.

4. The system of claim 1, wherein the air shield comprises a plurality of air jets.

5. The system of claim 1, wherein the air distribution apparatus produces the sanitized air from a height above an enclosed space including the person and one or more additional persons.

6. The system of claim 5, wherein the enclosed space comprises the person wearing the diffuser headband and one or more additional persons wearing the diffuser headband.

7. The system of claim 1, wherein the one or more diffusers comprise a substantially oval shape.

8. The system of claim 1, wherein the one or more diffusers are capable of swiveling about at least one of a horizontal axis and a vertical axis.

9. The system of claim 1, further comprising one or more additional diffuser headbands.

10. The system of claim 9, wherein the one or more additional diffuser headbands are worn by one or more additional persons occupying an enclosed space comprising the sanitized air generating source.

11. A diffuser headband apparatus, comprising:
    a solar adiabatic cooling vest;
    an elastic material comprising a substantially oval shape; and
    an elastic tube attached to the elastic material, wherein a first portion of the elastic tube comprises a plurality of apertures spaced along a surface of the elastic tube, wherein a second portion of the elastic tube comprises an inlet that receives sanitized air from the solar adiabatic cooling vest, wherein the plurality of apertures receive the sanitized air from the inlet and expel the sanitized air to provide an air shield that encircles a body of a person wearing the diffuser headband apparatus, and wherein the air shield blocks viral aerosol droplets generated by the person wearing the diffuser headband apparatus.

12. The apparatus of claim 11, wherein the air shield further blocks aerosol droplets within an enclosed space outside of the air shield from reaching the person wearing the diffuser headband.

13. The apparatus of claim 11, wherein the air shield comprises a plurality of air jets.

14. A diffuser headband system, comprising:
    a sanitized air generating source that produces sanitized air, wherein the sanitized air generating source comprises an air distribution apparatus coupled to one or more diffusers, the one or more diffusers comprising a perforated elastic tube, the perforated elastic tube comprising a plurality of apertures spaced along a surface of the elastic tube, the perforated elastic tube further comprising an inlet that receives the sanitized air from an outlet of the air distribution apparatus, wherein the plurality of apertures expel the sanitized air in a generally downward direction to provide an air shield by creating a 360-degree wall of air below the air distribution apparatus; and
    a diffuser headband formed from an elastic material comprising a substantially oval shape and an elastic tube attached to the elastic material, wherein a first portion of the elastic tube comprises a plurality of apertures spaced along a surface of the elastic tube, detachably coupled to the sanitized air generating source, wherein a second portion of the elastic tube comprises an inlet coupled to an outlet of the sanitized air generating source, wherein the inlet receives the sanitized air from the sanitized air generating source, wherein the plurality of apertures receive the sanitized air from the inlet and expel the sanitized air to provide an air shield comprising a plurality of air jets, wherein the plurality of air jets encircle a body of a person wearing the diffuser headband by creating another 360-degree wall of air, wherein the air shield blocks viral aerosol droplets generated by the person wearing the diffuser headband, and wherein the air shield further blocks viral aerosol droplets within an enclosed space outside of air shield from reaching the person wearing the diffuser headband.

* * * * *